United States Patent [19]

Rosenberg

[11] Patent Number: 4,690,139
[45] Date of Patent: Sep. 1, 1987

[54] DERMATOME PARTICULARLY USEFUL FOR SKIN-GRAFTING PURPOSES

[76] Inventor: Lior Rosenberg, 13 Harduf Street, Omer, Beer-Sheva, Israel

[21] Appl. No.: 869,830

[22] Filed: Apr. 30, 1986

Related U.S. Application Data

[63] Continuation of Ser. No. 588,778, Mar. 12, 1984, abandoned.

[30] Foreign Application Priority Data

Mar. 22, 1983 [IL] Israel .................................. 68193

[51] Int. Cl.⁴ ......................................... A61B 17/322
[52] U.S. Cl. ................................................. 128/305.5
[58] Field of Search ..................... 128/305.5, 305, 304, 128/751, 757

[56] References Cited

U.S. PATENT DOCUMENTS

| | | | |
|---|---|---|---|
| 2,579,029 | 12/1951 | Barker et al. | 128/305.5 |
| 3,221,744 | 12/1965 | Stryker | 128/305 |
| 3,428,045 | 2/1969 | Kratzsch et al. | 128/305.5 |
| 3,613,242 | 10/1971 | Hill et al. | 128/305.5 X |
| 4,270,540 | 6/1981 | Schwartz | 128/305.5 |

FOREIGN PATENT DOCUMENTS

| | | | |
|---|---|---|---|
| 641307 | 8/1950 | United Kingdom | 128/305.5 |
| 680029 | 10/1952 | United Kingdom | 128/305.5 |
| 240174 | 8/1969 | U.S.S.R. | 128/305.5 |

OTHER PUBLICATIONS

American V. Mueller Surgical Instruments Catalog, p. 1148, (1980).

*Primary Examiner*—Michael H. Thaler
*Attorney, Agent, or Firm*—Benjamin J. Barish

[57] ABSTRACT

A dermatome particularly useful for skin-grafting purposes comprises a guard for controlling the cutting depth, and an adjusting mechanism for effecting an angular displacement between the guard and the cutting depth, the guard extending the complete length of the cutting edge of the blade and being rounded at its opposite end enabling the full blade length to be used. The dermatome may be constructed with the guard, or the guard may be included in an accessory for attachment to the dermatome.

17 Claims, 17 Drawing Figures

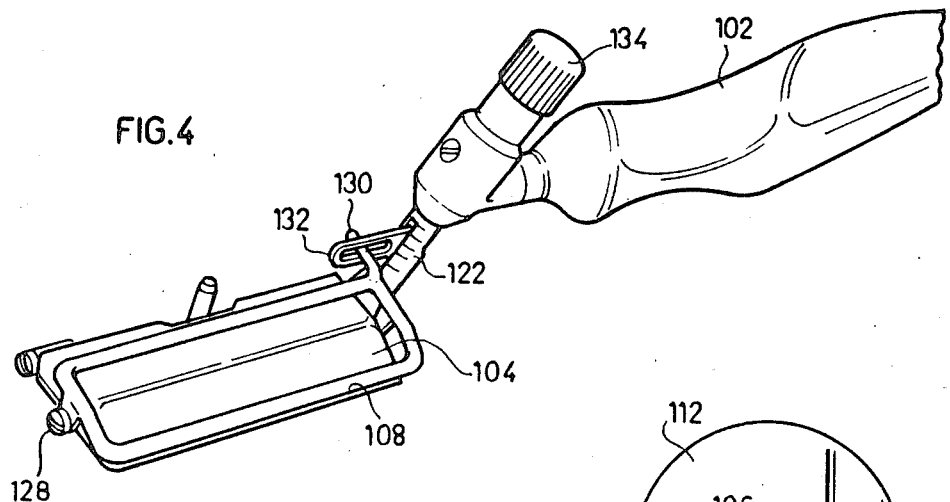
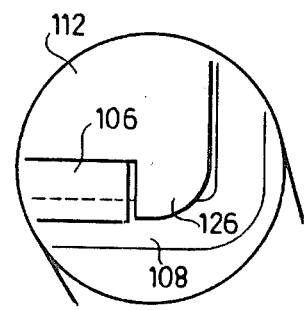
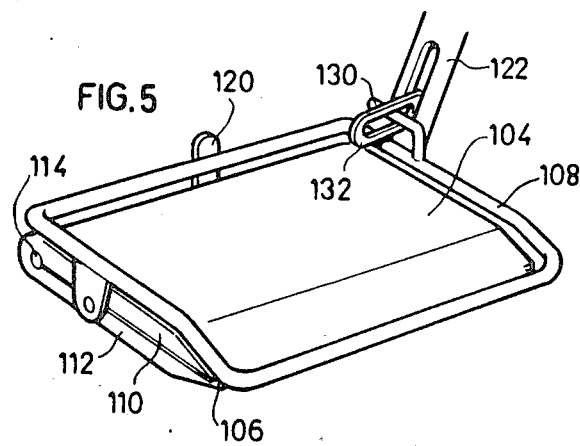
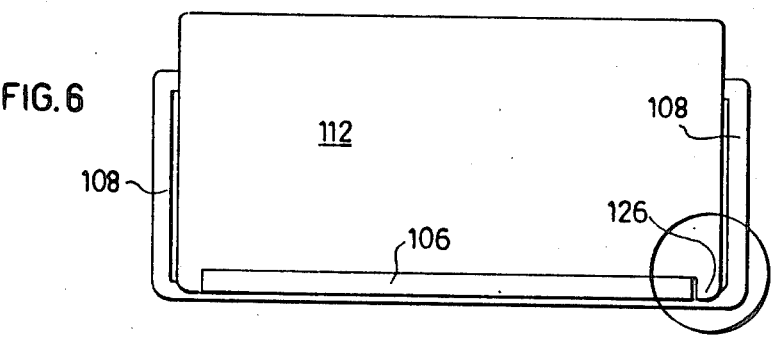

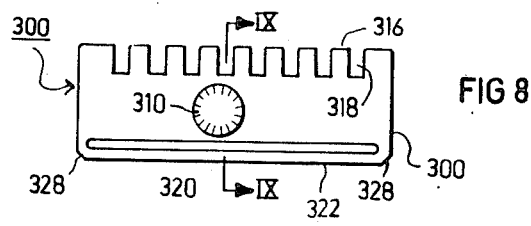
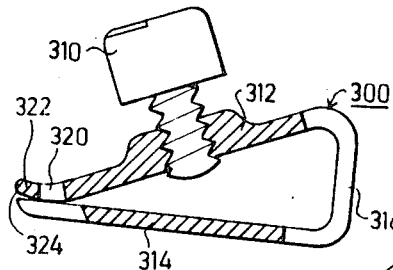
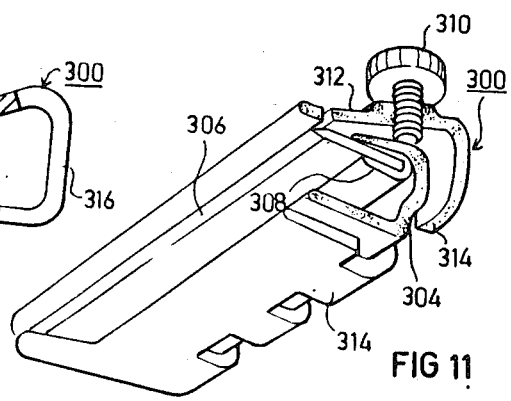
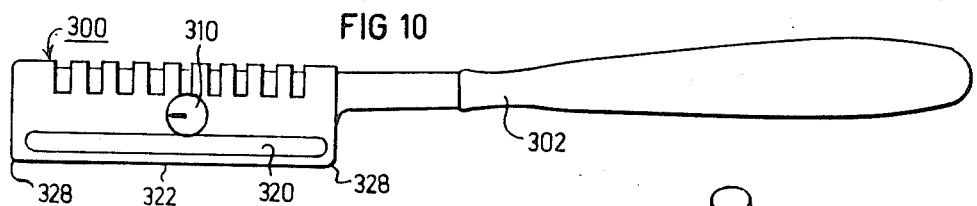
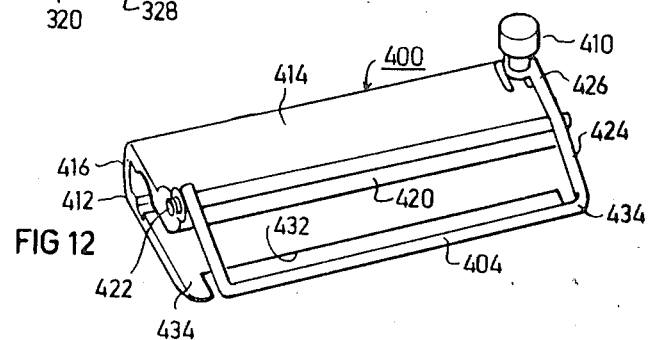

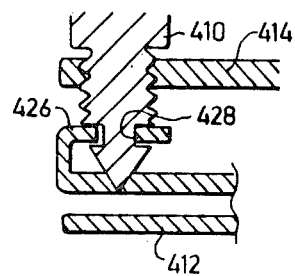
FIG.14
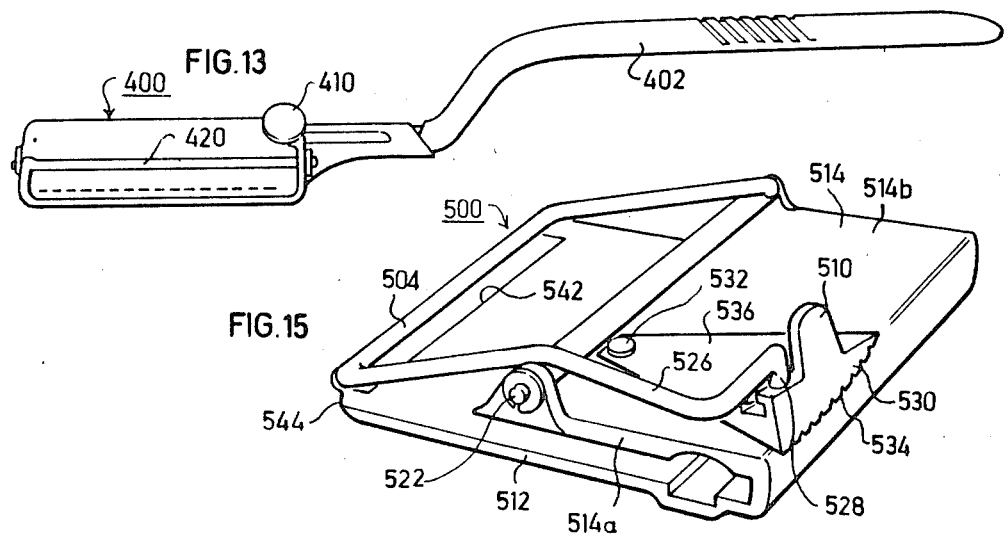
FIG.13
FIG.15
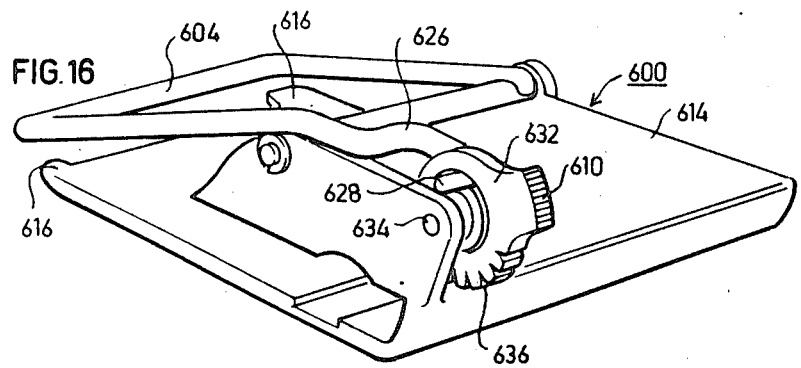
FIG.16

DERMATOME PARTICULARLY USEFUL FOR SKIN-GRAFTING PURPOSES

This application is a continuation of application Ser. No. 588,778, filed Mar. 12, 1984, now abandoned.

BACKGROUND OF THE INVENTION

The present invention relates to dermatomes particularly useful for cutting skin for grafting purposes.

The skin graft has become one of the commonly used techniques for the plastic surgeon particularly in the treatment of burns, skin defects and trauma. A number of dermatomes or instruments for cutting skin for grafting purposes have been proposed and are now in use, but none are entirely satisfactory for a number of reasons which will be particularly discussed below.

SUMMARY OF THE INVENTION

An object of the present invention is to provide a dermatome having improvements in those now in use for skin grafting purposes.

According to a broad aspect of the present invention, there is provided a dermatome comprising: a handle, a blade-mounting head for mounting a cutting blade; a guard for controlling the cutting depth; and adjusting means for effecting an angular displacement between the guard and the blade of the mounting head for varying the cutting depth; the guard extending the complete length of the cutting edge of the blade and being rounded at its opposite ends enabling the full blade length to be used during the reciprocation of the dermatome across the skin to be cut by the blade.

According to another feature of the invention, the blade mounting head is formed with projections at the ends protecting the corners of the cutting edge of the blade against catching the skin during the use of the cutting blade.

According to a still further feature of the invention, the handle is offset from the plane of the cutting blade; and according to a still further feature, the blade-mounting head includes means permitting the blade to be mounted from the underside of the head.

The guard may be incorporated in the dermatome as constructed, or may be supplied as a separate accessory for attachment to existing dermatomes. Several embodiments of each arrangement are described below for purposes of example.

BRIEF DESCRIPTION OF THE DRAWINGS

The invention is herein described with respect to several preferred embodiments, as illustrated in the accompanying drawings, wherein:

FIG. 4 is a three-dimensional view illustrating a medium-size dermatome constructed in accordance with the present invention;

FIG. 5 is an enlarged fragmentary view more particularly illustrating the structure of the dermatome of FIG. 4;

FIG. 6 is a top plan view, and FIG. 6a is an enlarged fragmentary view, illustrating the blade-mounting head in the dermatome of FIGS. 4 and 5, as well as that of FIGS. 1-3;

FIG. 8 illustrates a guard constructed in accordance with the invention as an accessory for attachment to an existing dermatome;

FIG. 9 is a transverse sectional view along lines IX—IX of FIG. 8;

FIG. 10 illustrates the guard of FIGS. 8 and 9 attached to an existing dermatome;

FIG. 11 is a fragmentary three-dimensional view more particularly illustrating the manner of attaching the guard of FIGS. 8 and 9 to the dermatome of FIG. 10;

FIG. 12 is a three-dimensional view illustrating another form of guard constructed in accordance with the invention as an accessory for attachment to an dermatome;

FIG. 13 illustrates the guard of FIG. 12 attached to a dermatome;

FIG. 14 is an enlarged fragmentary view better illustrating details of construction of the guard of FIG. 12; and FIG. 15 and 16 are three-dimensional views illustrating two further forms of guards constructed in accordance with the invention as accessories for attachment to existing dermatomes.

DESCRIPTION OF PREFERRED EMBODIMENTS

Figure 1:
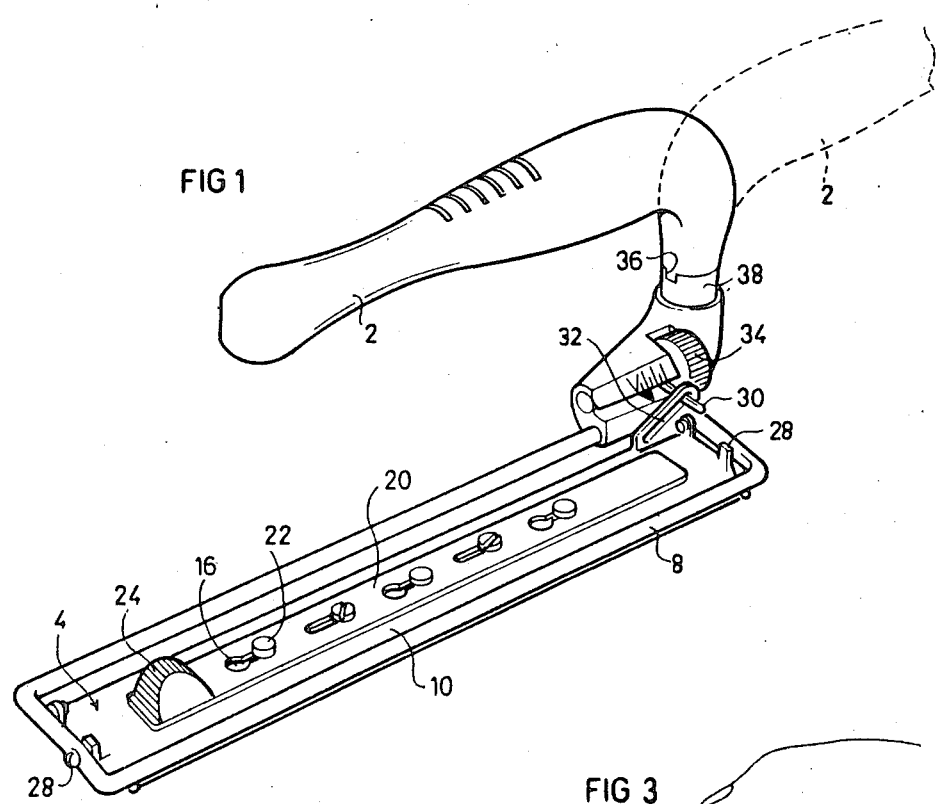
FIG. 1 is a three-dimensional view illustrating a large-size dermatome constructed in accordance with the present invention.
Figure 2:
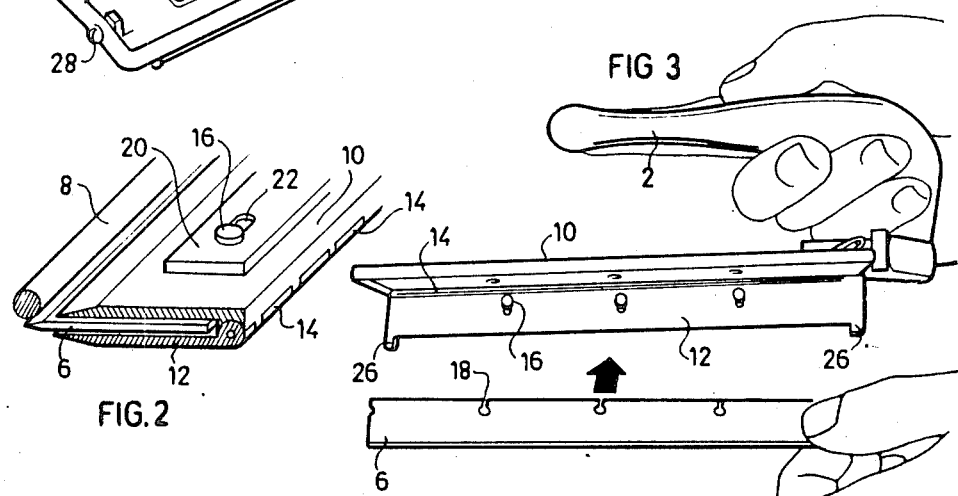
FIG. 2 is a fragmentary view, partly in section, more particularly illustrating the structure of the dermatome of FIG. 1.
Figure 3:
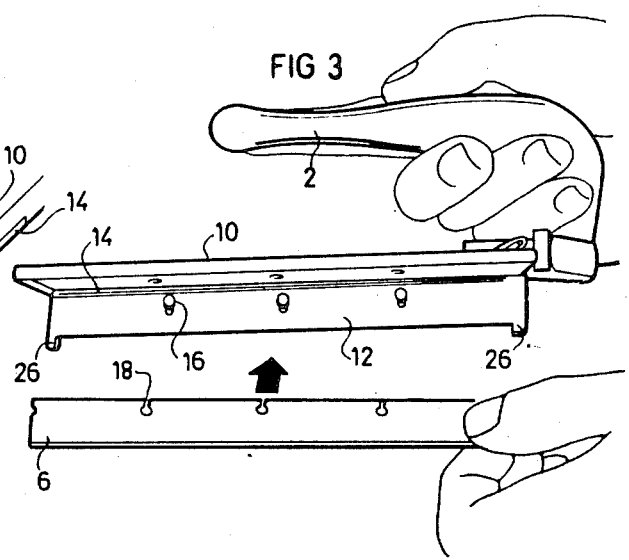
FIG. 3 illustrates the manner of loading the cutting blade from the underside of the dermatome of FIG. 1.

The Embodiment of FIGS. 1-3

The large-size dermatome illustrated in FIGS. 1-3 comprises a handle 2; a blade-mounting head, generally designated 4, for mounting a cutting blade 6 (FIGS. 2 and 3); and a guard 8 which is pressed against the skin to control the cutting depth. In the embodiment of FIG. 1, the blade-mounting head 4 is angularly adjustable, in the manner to be described below, with respect to the guard 8 in order to vary the depth cut by blade 6 mounted in the head 4.

As shown particularly in FIGS. 2 and 3, the blade-mounting head 4 comprises two plates, namely a top plate 10 pivotably mounted to a base plate 12 by means of hinges 14 extending along the rear side of the mounting head, i.e., the side opposite to that through which the cutting blade 6 projects. The base plate 12 is provided with a plurality of pins 16 receivable within openings 18 formed along the rear edge of the cutting blade 6. Thus, the cutting blade 6 may be loaded from underneath the mounting head 4 by pivoting the base plate 12 to its open position, as shown in FIG. 3, inserting the cutting blade 6 therein with its openings 18 received over the pins 16, and then pivoting the base plate 12 to its closed position as illustrated in FIG. 2 with the cutting edge of blade 6 projecting through the front edge of the mounting head. For locking the base plate in its closed position, a locking plate 20 provided with bayonet slots 22 is slidably mounted on the upper face of the top plate 10, and is slid, by the aid of the finger button 24 (FIG. 1), axially of the mounting head in order to move its bayonet slots 22 into locking engagement with pins 16 carried by the base plate 12.

The guard 8 is in the form of a rod of cylindrical cross-section and completely circumscribes the blade-mounting head 4. The corners of the guard are rounded, as shown particularly in FIG. 1. This arrangement as illustrated particularly in FIG. 1, wherein the guard 8 extends the complete length of the cutting blade 6 and is rounded at its opposite ends, provides an important advantage to this type of dermatome in that it enables the full blade length to be used.

Another advantage provided by this dermatome is more particularly illustrated in FIG. 3, wherein it will be seen that the base plate 12 of the blade-mounting head 4 is formed with projections 26 at its opposite ends. These projections protect the corners of the cutting blade 6 against catching the skin during the use of the dermatome.

In the arrangement of FIG. 1, the guard 8 is fixed to the handle 2, and the blade-mounting head 4 is angularly movable with respect to the guard in order to vary the cutting depth by the blade 6 carried by the head. For this purpose, the blade-mounting head 4 is pivotably mounted to the guard 8 at opposite pivot points 28 (FIG. 1) and is pivoted by means of a pin and slot arrangement including a pin 30 carried by the handle 2, and a slotted member 32 carried by the guard 8. As shown in FIG. 1, the slotted plate 32 is fixed at an angle, e.g., about 45°, to the plane of the guard 8, whereas pin 30 is displaceable within the slot of member 32, by rotating the micrometer screw 34, substantially parallel to the plane of the guard. Thus, as pin 30 is displaced leftwardly in FIG. 1, it will cause the blade-mounting head 4 to pivot to a larger angle with respect to the plane of the guard 8; and as the pin is displace rightwardly, it will pivot the head 4 to a smaller angle with respect to the guard.

Handle 2 is shaped so as to provide a comfortable grip by the surgeon. This handle is pivotally mounted to either the illustrated full-line position of FIG. 1, wherein it overlies the blade-mounting head 4, or to the broken-line position wherein it is disposed laterally of the blade-mounting head but offset from the plane of the head. Handle 2 may be retained in either of the above two positions by means of a retainer rib 36 received within a slot formed in socket 38 for the handle. Thus, to change the handle from one position to the other, it is only necessary to pull out the handle slightly from the socket 38 against the action of a spring (not shown), rotate the handle to the desired position, and then release it, whereupon its internal spring will cause its rib 36 to seat within the recess formed in the socket 38.

The above-described handle construction provides a number of important advantages. One particularly important advantage is that, since the handle is offset from the plane of the cutting blade in both positions of the handle, the surgeon's hand is removed from the operation field, and thereby avoids obstructing this field. In addition, this handle arrangement provides a much improved mechanical leverage for greater control of blade angle and pressure, and also enables the surgeon to use his stronger forearm muscles for applying the pressure, leaving the finger muscles for fine control. Further, the pivotal arrangement of the handle 2 not only facilitates its use by the surgeon for any particular application, but also enables the device to be used equally as well by a left-hand surgeon or by a right-hand surgeon.

Still further, the pin and slot arrangement (members 30, 32) provides a simple and convenient means for adjusting the angle of the cutting blade with respect to the guard, while assuring that the guard will always remain parallel with the cutting edge of the blade.

The Embodiment of FIGS. 4–6

The dermatome illustrated in FIGS. 4–6 is particularly useful as a medium-size instrument for cutting skin for grafting purposes and provides a number of the same advantages as the dermatome illustrated in FIGS. 1–3. Thus, the dermatome of FIGS. 4–6 also includes a handle 102 which is offset from the plane of the cutting blade carried by a mounting head 104. The dermatome of Figs. 4–6 further includes a rectangular guard 108 of cylindrical cross-section. Guard 108 also extends the complete length of the cutting blade 106 and is rounded at its opposit.e ends, as shown particularly in FIG. 6, thereby also enabling the full blade length to be used.

As shown particularly in FIG. 5, the blade-mounting head 104 in the dermatome of FIGS. 4–6 also includes a top plate 110 to which is pivotably mounted a base plate 112 by means of hinges 114 extending along the rear side of the mounting head, i.e., the side opposite to the cutting blade 106. As shown particularly in FIGS. 6 and 6a, the base plate 112 is also provided with the end projections 126, corresponding to projections 26 in FIG. 3, which protect the blade corners against catching the skin during use of the dermatome.

The dermatome illustrated in FIGS. 4–6 is also loaded from underneath as in the dermatome of FIGS. 1–3, by pivoting the base plate 112 downwardly to permit the insertion of the cutting blade 106, whereupon the base plate is then pivoted back against the top plate 110. However, in the dermatome of FIGS. 4–6, the base plate 112 is retained closed by means of a retainer latch 120 fixed to the base plate and releasably engageable with the rear side of the guard 108.

Another variation in the dermatome of FIGS. 4–6, over that of FIGS. 1–3, is in the manner of angularly adjusting the guard 108 with respect to the blade 106 carried by the mounting head 104 in order to vary the cutting depth. Thus, in the arrangement of FIGS. 4–6, the top plate 110 of the blade-mounting head 104 is secured to the handle 102 by means of a stem 122, and the guard 108 is pivotably mounted to the top plate 110 at pivot points 128 at the opposite ends of the guard. A similar pin-and-slot arrangement is also used for adjusting the guard with respect to the cutting blade, but in this case the pin 130 is secured to the guard 108, and the slotted plate 130 is carried by the handle 102 and is movable along its stem 122 by means of the micrometer screw 134. Stem 122, and therefore slotted plate 132, is at an angle (e.g., about a 45° angle) with respect to the guard 108, so that the movement of the slotted plate 132 up and down within stem 122 will cause the guard 108 to pivot with respect to the top plate 110 of the mounting head 104, and thereby with respect to the cutting blade 106 carried by the head.

Figure 7:
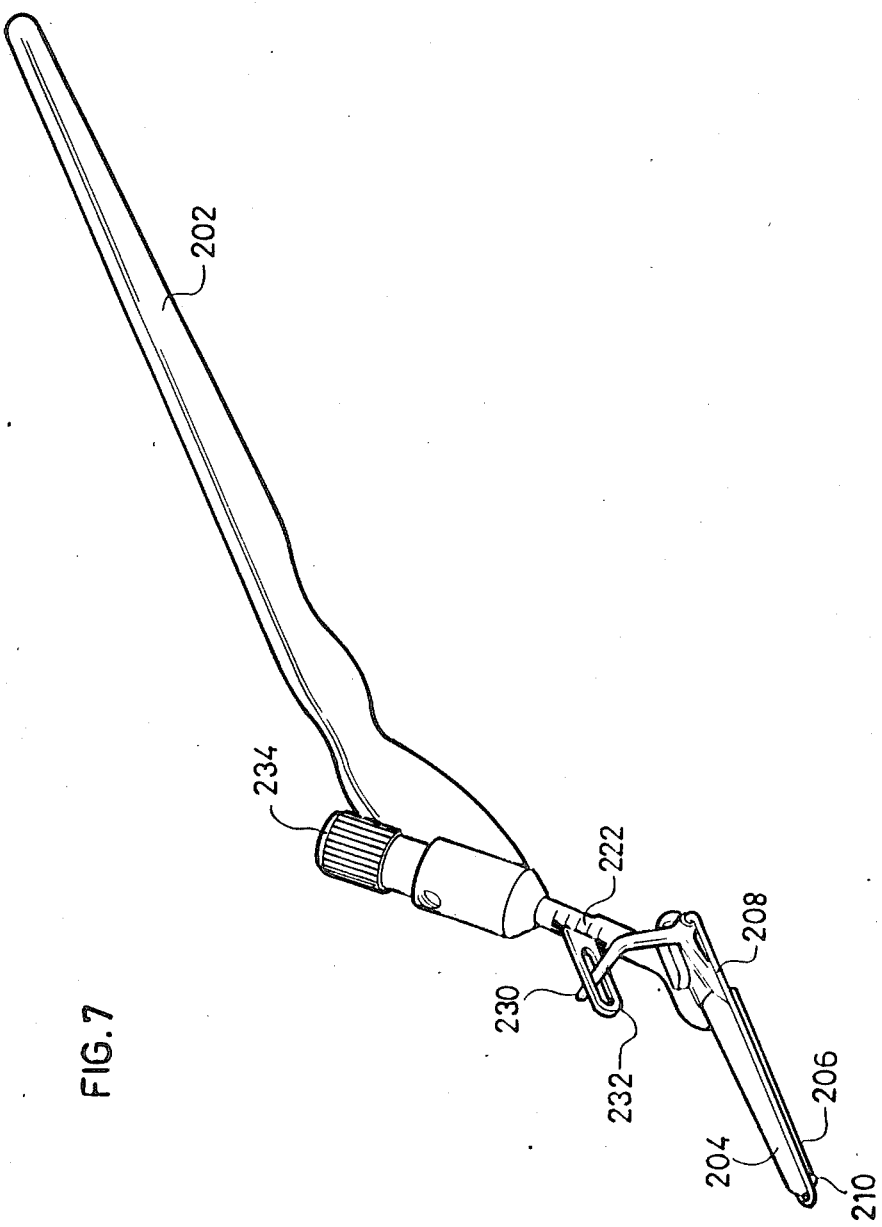
FIG. 7 is a three-dimensional view illustrating a small-size dermatome constructed in accordance with the present invention.

The Embodiment of FIG. 7

FIG. 7 illustrates a small form of dermatome including many of the features of the two dermatomes described above. Thus, the dermatome illustrated in FIG. 7 also includes a handle 202 offset from the plane of the cutting blade 206 carried by the blade-mounting head 204, and a guard 208 extending the complete length of the blade and rounded at its opposite ends to enable the full blade length to be used. The blade 206 in the FIG. 7 dermatome is also loaded from underneath, but in this case the blade-mounting head 204 is constituted only of a single member formed with pins 210 projecting from its bottom face, which pins are received within bayonet slots formed in the cutting blade, similar to slot 22 formed in the locking plate 20 in the FIG. 1 construction.

The FIG. 7 dermatome also includes a pin-and-slot arrangement for varying the angle of the cutting blade 206 with respect to the guard 208, this arrangement being somewhat similar to that of FIGS. 4–6. Thus, in the dermatome of FIG. 7, the blade-mounting head 204 is fixed to the handle 202 by means of an angular stem 222, and the guard 208 carries the pin 230 received within the slotted plate 232. The slotted plate is movable up and down by micrometer screw 234 to thereby vary the angle of the guard 208 with respect to the cutting blade 206, to control the depth of cutting.

The foregoing embodiments of the invention illustrate the guard constructed as part of the dermatome. As indicated earlier, the guard may be constructed as an accessory for attachment to the existing dermatomes, and several embodiments of such constructions are illustrated in FIGS. 8–16.

The Embodiment of FIGS. 8–11

FIGS. 8–11 illustrate one form of accessory, generally designated 300, for attachment to an existing dermatome 302 (FIG. 10), the latter being shown as of the known Goulian type commonly used for skin grafts. This dermatome is typically supplied with a set of replaceable blades and a depth guage and guard (not shown) attachable to the dermatome for controlling the cutting depth. However, such guards are not provided with means for varying the angular displacement between the guard and the blade for varying the cutting depth. Accessory 300 illustrated in FIGS. 8–11 may thus be used with the conventional dermatome 302 in place of the guard commonly provided for such dermatomes.

The known Goulian-type dermatome 302 includes a blade holder 304 (FIG. 11) for mounting the blade 306, the latter being formed with a thickened spine 308 along its edge opposite to the cutting edge receivable within the blade holder. Accessory 300 is in the form of a blade-mounting head mountable to the blade holder 304 by means of a threaded screw 310 threaded through the upper wall of the head and engageable with the blade holder 304 of the dermatome.

The construction of blade-mounting head 300 is more particularly illustrated in FIG. 9, and the manner of mounting same onto the blade holder 304 of the dermatome 302 is best illustrated in FIG. 11. Thus, as shown in FIG. 9, blade-mounting head 300 comprises an upper wall 312 joined to a lower wall 314 by a web portion 316 formed with a plurality of slots 318 imparting resiliency to the web. The upper wall 312 is formed at an angle, e.g. about 45°, to the lower wall 314. The end of the upper wall 312 opposite to web 316 is formed with an elongated slot 320 extending parallel to, and for substantially the complete length of, the outer free end of wall 312. This free end of wall 312 is rounded along its upper and lower edges, as shown at 324 (FIG. 9), and the opposite ends of wall 312 are also rounded, as shown at 328 in FIG. 8. Thus, portion 322 of wall 312 defines a guard extending the complete length of the cutting edge of the blade 306 which guard is rounded at its opposite ends, thereby enabling the full blade length to be used, as in the previously-described embodiments. In addition, the lower wall 314 is formed with end projection 326 (FIG. 11) corresponding to end projections 26 in FIG. 3 for example, which protect the corners of the cutting edge of the blade against catching the skin during use of the cutting blade.

As also in the previously-described embodiments, guard 322 may be angularly displaced with respect to the blade 306 in order to vary the cutting depth. In the accessory of FIGS. 8–10, this angular displacement of the guard is effected by screw 310. Head 300 is attachable to blade 306 of the dermatome primarily by the inherent resiliency of web 316 connecting together its two walls 312, 314, and is firmly secured to the blade by screw 310 engaging blade holder 304. Guard 322 of the head is angularly adjustable with respect to the blade by rotating screw 310, which screw, by engaging the blade holder 304, varies the angle of guard 322 with respect to the blade for varying the cutting depth.

The Embodiment of FIGS. 12–14

FIGS. 12–14 illustrate an accessory, generally designated 400, also in the form of a blade-mounting head for mounting to an existing dermatome, which in this case is a Swann-Morton type dermatome, generally designated 402, also commonly used for skin-graft operations. In this embodiment of the invention, the guard is not integral with the head, as in the embodiment of FIGS. 8–11, but rather is in the form of a cylindrical rod 404 extending the complete length of the cutting edge of the blade and adapted to be angularly displaced with respect to it for varying the cutting depth.

Thus, head 404 in FIGS. 12–14 also includes a lower wall 412 joined to an upper wall 414 by a resilient web 416 permitting the head to be attached to the blade of the dermatome 402, as shown in FIG. 13. Guard 404 is integrally formed with another cylindrical rod 420 extending parallel to the guard, which rod is pivotably mounted at 422 to the upper wall 414 of the head. Guard 404 further includes an arm 424 at one end, which arm terminates in an eye 426 received within an annular groove 428 formed in the shank of screw 410 threaded through the top wall 414 of the head 400. In addition, the lower wall 412 of the head is formed with a slot 432 extending substantially the complete length of the wall but terminating short of its opposite ends so as to define projections 434 at the ends of the head protecting the corners of the cutting edge of the blade against catching the skin during the use of the dermatome, similar to projections 126 in FIGS. 6 and 6a.

Head 400 may thus be attached to the blade of the dermatome 402 by the resiliancy of web 416 joining the opposite walls 412, 414 of the head, such that rod 404 serves as a guard extending the complete length of the cutting edge of the blade. The end of screw 410 is engageable with the cutting blade (i.e., the edge of the blade holder as shown at 304 in FIG. 11), such that the screw serves not only for firmly securing the head to the dermatome, but also for effecting the angular adjustment of the guard with respect to the blade for varying the cutting depth. In addition, projections 434 at the ends of walls 412 of the head 400 protect the corners of the cutting edge of the blade against catching the skin during the use of the dermatome.

The Embodiments of FIGS. 15 and 16

FIGS. 15 and 16 illustrate two further heads constructed as accessories for attachment to existing dermatomes, which heads are similar to the construction of FIGS. 12–14 but include different arrangements for varying the angular position of the guard with respect to the blade for varying the cutting depth.

Thus, the head illustrated in FIG. 15, and therein generally designated 500, includes a guard 504 corresponding to guard 404 in FIGS. 12-14, but in this case the angular position of the guard is adjustable by a wedge 510 pivotally mounted at 532 to the top wall 514 of the head, and formed with a ribbed or knurled edge 534 frictionally engaging the top wall. As in FIGS. 12-14, guard rod 504 is pivotally mounted at 522, and includes an arm 526 terminating in an eye 528 receiving wedge 530. The top wall 514 is inclined with respect to the lower wall 512 such that one end 514a is closer to wall 512 than the opposite end 514b. In addition, arm 536 pivotally mounting wedge 530 to the pivot point 532 is resilient, permitting the wedge to be displaced towards or away from the lower wall 512 of the head, as wedge 530 is moved about pivot point 532 along the upper wall 514.

In all other respects, head 500 of FIG. 15 is constructed the same as head 400 in FIGS. 12-14, including slot 542 formed in the bottom wall 512 to define the projections 544 for protecting the corners of the cutting edge of the blade. Thus, head 500 illustrated in FIG. 15 is mounted and used in substantially the same manner as head 400 illustrated in FIGS. 12-14, except that the angular adjustment of guard 504 is effected by pivoting wedge 530 on its pivot point 532.

FIGS. 16 illustrates an arrangement similar to that of FIG. 15, wherein the head, therein designated 600, includes an eccentric wheel 610 for adjusting the angular position of the guard 604 with respect to the blade when the head is mounted to an existing dermatome. Thus, guard 604 is also formed with an arm 626 terminating in an eye 628, but in this case, the eye is received within an eccentric slot 632 formed in wheel 610, the latter being pivotally mounted at 634 to the upper wall 614 of the head. The lower face of the wheel 610 is also ribbed or knurled to frictionally hold the wheel in any adjusted position, it being thus seen that by rotating wheel 610 about its pivot 634, it adjusts the angular position of the guard 604 with respect to the blade (not shown) when the head 600 is mounted to an existing dermatome. In this case, as in the previously-described embodiments, the blade-mounting head 600 also includes the end projections 616 (FIG. 16) to protect the corners of the blade against catching the skin.

While the invention has been described with respect to a number of preferred embodiments, it will be appreciated that these are shown for purposes of example, and that many other variations, modifications, and applications of the invention may be made.

What is claimed is:

1. A dermatome, comprising: a handle; a blade-mounting head for mounting a cutting blade; a guard for controlling the cutting depth; and adjusting means for effecting an angular displacement between aid guard and the blade of the mounting head for varying the cutting depth; said guard being carried by said blade-mounting head so as to be movable therewith during the reciprocation of the blade-mounting head and extending the complete length of the cutting edge of the blade; said guard being rounded at its opposite ends enabling the full blade length to be used during the reciprocation of the head, blade and guard across the skin to be cut by the blade; said blade-mounting head being formed with projections at the ends protecting the corners of the cutting edge of the blade against catching the skin during use of the cutting blade.

2. The dermatome according to claim 1, wherein said handle is offset from the plane of the cutting blade.

3. The dermatome according to claim 1, wherein said blade-mounting head includes maans permitting the blade to be mounted from the underside of the head.

4. The dermatome according to claim 1, wherein said blade-mounting head comprises a top plate and a base plate hinged to the top plate along the rear side of the blade-mounting head, permitting the base plate to be pivoted to its open position for the insertion of a blade from the underside of the head.

5. The dermatome according to claim 4, wherein said base plate is formed with pins receivable in holes in the cutting blade.

6. The dermatome according to claim 5, further including a locking plate slidable laterally over the top plate and formed with bayonet slots for locking the base plate in its closed position with respect to the top plate.

7. The dermatome according to claim 4, wherein said base plate is formed with a resilient latch releasably engageable with the top plate for latching same in its closed position.

8. The dermatome according to claim 1, wherein said handle is offset from the plane of the blade-mounting head and is pivoted from a first position overlying said blade-mounting head, to a second position extending laterally of, but offset from, the blade-mounting head.

9. The dermatome according to claim 1, wherein said adjusting means comprises a pin member and a slotted member receiving said pin member, one of said members being fixed to said blade-mounting head, and the other being fixed to said guard, said adjusting means including means for moving one of said members with respect to the other member to thereby effect said angular displacement between the blade-mounting head and the guard.

10. The dermatome according to claim 9, wherein said guard is fixed to said handle, and said slotted member is fixed to said blade-mounting head at an angle to said pin member, said pin member being adjustable on said handle to move along said slotted member and thereby to adjust the angle of said blade-mounting head with respect to said guard.

11. The dermatome according to claim 10, wherein said guard is in the form of a cylindrical rod circumscribing said blade-mounting head.

12. The dermatome according to claim 11, wherein said blade-mounting head is pivotably mounted at its opposite ends to said guard.

13. The dermatome according to claim 9, wherein said blade-mounting head is fixed to said handle, and said pin member is fixed to said guard, said slotted member being adjustable on said handle to move said pin member received therein, and thereby to adjust the angle of said blade-mounting head with respect to said guard.

14. An accessory for attachment to a dermatome including a handle and a blade holder, said accessory comprising a blade-mounting head attachable to said blade holder, and a guard for controlling the cutting depth, said guard being carried by said blade-mounting head so as to be movable therewith and extending the complete length of the cutting edge of the blade, said guard being rounded at its opposite ends enabling the full blade length to be used during the reciprocation of the blade-mounting head, blade and guard across the skin to be cut by the blade; said blade-mounting head being formed with projections at the ends protecting the corners of the cutting edge of the blade against catching the skin during use of the cutting blade; and adjusting means for effecting an angular displacement between said guard and the blade of the dermatome when the accessory is mounted thereon, for varying the cutting depth.

15. The accessory according to claim 14, wherein said accessory further includes a mounting head for mounting on the cutting blade of the dermatome.

16. The accessory according to claim 5, wherein said guard is integrally formed with said mounting head.

17. The accessory according to claim 15, wherein said guard is in the form of a cylindrical rod extending the complete length of the cutting edge of the blade, when the accessory is mounted to said dermatome, said adjusting means angularly displacing said cylindrical rod with respect to said mounting head.

* * * * *